United States Patent [19]
Gottesman et al.

[11] Patent Number: 5,710,014
[45] Date of Patent: Jan. 20, 1998

[54] CLONED CDNA FOR HUMAN PROCATHEPSIN L.

[75] Inventors: Michael M. Gottesman, Bethesda, Md.; Susannah Gal, Basel, Switzerland; Spencer Smith, Kensington, Mass.

[73] Assignee: The United States of America as represented by the Department of Health and Human Services, Washington, D.C.

[21] Appl. No.: 158,075

[22] Filed: Nov. 24, 1993

Related U.S. Application Data

[63] Continuation of Ser. No. 904,400, Mar. 11, 1992, abandoned, which is a continuation of Ser. No. 154,692, Feb. 11, 1988, abandoned.

[51] Int. Cl.[6] .................... C12N 15/52; C12N 15/63; C12N 15/65; C12N 15/70

[52] U.S. Cl. .................... 435/68.1; 435/91; 435/172.3; 435/235.1; 435/240.2; 435/252.3; 435/255.1; 435/254.21; 536/23.2; 536/23.5; 530/350; 935/9; 935/18; 935/32; 935/41; 935/57; 935/61; 935/71

[58] Field of Search .................... 435/68.191, 172.3, 435/235.1, 320.1, 252.3, 240.2, 255, 256, 255.1; 536/23.2, 23.5; 530/350; 935/9, 18, 32, 41, 57, 61, 71

[56] References Cited

PUBLICATIONS

Joseph et al. J. Clin. Invest. 81:1621–1629 May 1988.
Yang etal Nucl. Acids Res vol. 12 pp. 837–843 (1984).
Woods etal. J. Clin. Invest. vol. 74 pp. 634–638 (1984).
Masar et al Biochem J. vol. 240 pp.373–377 (1986).
Suggs et al Proc Natl Acad Sci USA vol. 78 pp. 6613–6617 (1981).
Partnoy et al J. Biol Chem vol. 261 pp 1497–14703 (1986).
Masor et al Chemical Abstracts vol. 105 p. 360 Abstract No. 22175a (1886).
Maniatis, T. et al Molecular Clarity, A Laboratory Manual Cold Springs Herbor Laboratory CSH; NY (1982).
Ueda, K et al Proc Nat'l Acad Sci USA vol. 84 pp. 3004–3008 (1987).
Gottsman, "Transformantion–dependent Secretion of a Low Molecular Weight . . . ", Proc. Natl. Acad. Sci. USA, 75:2767–2771 (Jun. 1978).
Doherty, et al., "Malignant Transformation and Tumor Promoter . . . ", Molecular and Cellular Biology, 5:466–473 (Mar., 1985).
Troen, et al., "Sequence and Expression of the cDNA for MEP (Major Excreted Protein) . . . ", Biochem J., 731–735, Great Britain (1987).

Primary Examiner—Anthony C. Caputa
Attorney, Agent, or Firm—Morgan & Finnegan

[57] ABSTRACT

A cloned cDNA containing complete coding sequence for the expression of a protein with all properties of the precursor to human procathepsin L is described. All of the protein's major domains, including the pre, pro, and carboxyterminal extensions are represented in the full length cDNA sequence of the present invention.

12 Claims, 5 Drawing Sheets

FIG. 1B

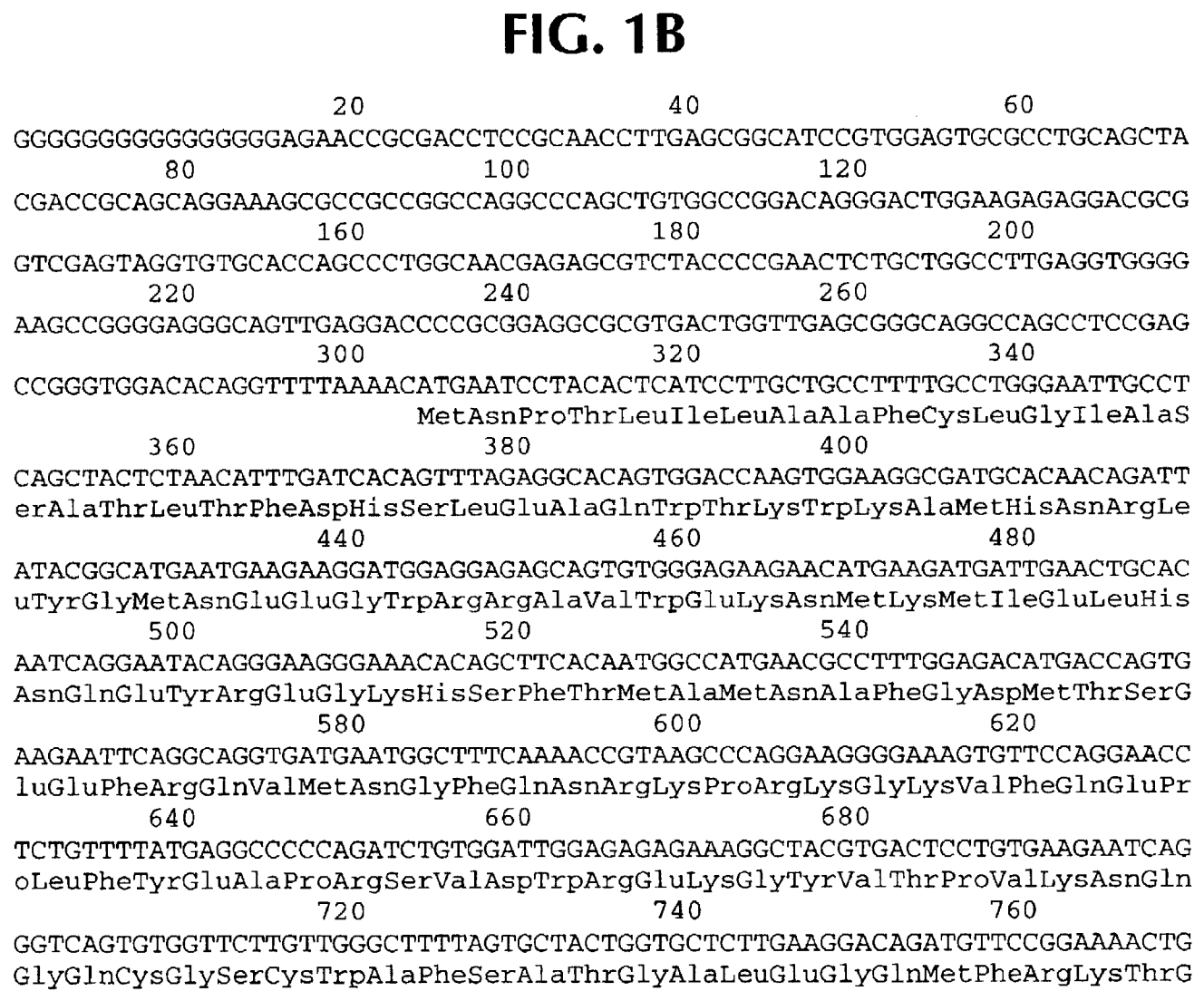

```
                    20                    40                    60
GGGGGGGGGGGGGGGAGAACCGCGACCTCCGCAACCTTGAGCGGCATCCGTGGAGTGCGCCTGCAGCTA
          80                   100                   120
CGACCCGCAGCAGGAAAGCCCCGCCCAGGCCCAGCTGTGGCCCGGACACAGGAGACTGGAAGAGAGGACGCG
         160                   180                   200
GTCGAGTAGGTGTGCACCAGCCCTGGCAACGAGAGCGTCTACCCCGAACTCTGCTGGCCTTGAGGTGGGG
         220                   240                   260
AAGCCGGGAGGGCAGTTGAGGACCCCGCGGAGGCGCGTGACTGGTTGAGCGGGCAGGCCAGCCTCCGAG
         300                   320                   340
CCGGGTGGACACAGGTTTAAAAACATGAATCCTACACTCCTTGCTGCCTTTTGCCTGGGAATTGCCT
                                  MetAsnProThrLeuIleLeuAlaAlaPheCysLeuGlyIleAlaS
         360                   380                   400
CAGCTACTCTAACATTTGATCACAGTTTAGAGGCACAGTGGACCAAGTGGAAGGCGATGCACAACAGATT
erAlaThrLeuThrPheAspHisSerLeuGluAlaGlnTrpThrLysTrpLysAlaMetHisAsnArgLe
         440                   460                   480
ATACGGCATGAATGAAGAAGGATGGAGAGCAGTGTGGGAGAAGAACATGAAGATGATTGAACTGCAC
uTyrGlyMetAsnGluGluGlyTrpArgAlaValTrpGluLysAsnMetLysMetIleGluLeuHis
         500                   520                   540
AATCAGGAATACAGGAGTGATGAATGGCTTTCAAAACCGTTCACAATGGCCATGAATGCCTTTGGAGACATGACCAGTG
AsnGlnGluTyrArgGluGluLysHisSerPheThrMetAlaMetAsnAlaPheGlyAspMetThrSerG
         580                   600                   620
AAGAATTCAGGCAGGTCAGGTCAGCTTCACAAACCGTAAGCCCAGGAGGGAAAGTGTTCCAGGAACC
luGluPheArgGlnValMetAsnGlyPheGlnAsnArgLysProArgLysGlyLysValPheGlnGluPr
         660                   680
TCTGTTTTATGAGCAGATCTGTGATGGGCTTTTAGTGCTACTGGTGCTCTTGAAGGACAGATGTTCCGGAAAACTG
oLeuPheTyrGluAlaProArgSerValAspTrpArgGluLysGlyTyrValThrProValLysAsnGln
         720                   740                   760
GGTCAGTGTGGTTCTTGTTGGGCTTTTAGTGCTACTGGTGCTCTTGAAGGACAGATGTTCCGGAAAACTG
GlyGlnCysGlySerCysTrpAlaPheSerAlaThrGlyAlaLeuGluGlyGlnMetPheArgLysThrG
```

FIG. 1C

```
       780              800              820
GGAGGCTTATCTCACTGAGTGAGCAGAGAATCTGTAGACTGCTCTGGGCCTCAAGGCAATGAAGGCTGCAA
lyArgLeuIleSerLeuSerGluGlnAsnLeuValAspCysSerGlyProGlnGlyAsnGluGlyCysAs
                              860              880              900
TGGTGCCTAATGGATTATGCTTTCCAGTATGTTCAGGATAATGGAGGCCTGGACTCTGAGGAATCCTAT
nGlyGlyLeuMetAspTyrAlaPheGlnTyrValGlnAspAsnGlyGlyLeuAspSerGluGluSerTyr
             920              940              960
CCATATGAGGCAACAGAAGAATCCTGTAAGTACAATCCCAAGTATTCTGTTGCTAATGACACCGGCTTTG
ProTyrGluAlaThrGluGluSerCysLysTyrAsnProLysTyrSerValAlaAsnAspThrGlyPheV
       980             1000             1020             1040
TGGACATCCCTAAGCAGGAGAAGGCCCTGATGAAGGCAGTTGCAACTGTGGGGCCCATTCTCTGTTGCTAT
alAspIleProLysGlnGluLysAlaLeuMetLysAlaValAlaThrValGlyProIleSerValAlaIl
              1060             1080             1100
TGATGCAGGTCATGAGTCCTGTTCCTCTATAAAGAAGGCATTTATTTGAGCCAGAATGTAGCAGTGAA
eAspAlaGlyHisGluSerPheLeuPheTyrLysGluGlyIleTyrPheGluProAspCysSerSerGlu
        1120             1140             1160             1180
GACATGGATCATGGTGTGCTGGTGGTTGGCTACGGATTTGAAAGCACAGAATCAGATAACAATAAATATT
AspMetAspHisGlyValLeuValGlyValGlyLeuAsnSerTyrProAsnAsnLysTyrT
             1200             1220             1240
GGCTGGTGAAGAACAGCTGGGGTGAAGAATGGGGCATGGGTGGCTACGTAAAGATGGCCAAAGACCGGAG
rpLeuValLysAsnSerTrpGlyGluTrpGlyMetGlyTrpValLysMetAlaLysAspArgAr
       1260             1280             1300             1320
AAACCATTGTGGAATTGCCTCAGCAGCCAGCTACCCCACTGTGTGAGCTGGTGGACGGTGATGAGGAAGG
gAsnHisCysGlyIleAlaSerAlaAlaSerTyrProThrValend
             1340             1360             1380
ACTTGACTGGGGATGGCCATGGCATGGCAATTCATCTTCAGTCTTCAGTCCTACCAGCCCCCGCTGTCGGATA
              1400             1420             1440             1460
CACACTCGAATCATTGAAGATCCGAGTGTGATTGAATTCTGTGATATTTTCACACTGGTAAATGTTACC
              1480             1500             1520
TCTATTTTAATTACTGCTATAAATAGTTTATATTATTGATTCACTTACTGACTTTGCATTTTCGTTTTT
             1540             1560             1580
AAAAGGATGTATAAATTTTTACCTGTTTAAATAAAATTTAATTTCAAATGTAAAAAAAAAAAAAAAAAAA
```

FIG. 2

```
              10      ↓ 20        30          40
mouse    MNLLLLLAVLCLGTALATPKFDQTFSAEWHQWKSTHRRLYGTNEEE
         ||  |:||: ||| | || ||  :  | |  || |  |||| |||
human    MNPTLILAAFCLGIASATLTFDHSLEAQWTKWKAMHNRLYGMNEEG
              10        20        30         40

50          60          70        80         90
WRRAIWEKNMRMIQLHNGEYSNGQHGFSMEMNAFGDMTNEEFRQVVNGYRHQK
||||:|||||:||  ||| ||   | | |:| |||||||| |||||| ||:  |
WRRAVWEKNMKMIELHNQEYREGKHSFTMAMNAFGDMTSEEFRQVMNGFQNRK
 50        60         70        80        90

110        120         130       140         150
HKKGRLFQEPLMLKIPKSVDWREKGCVTPVKNQGQCGSCWAFSASGCLEGQMF
:||::|||||         |:|||||||| ||||||||||||||||:| ||||||
PRKGKVFQEPLFYEAPRSVDWREKGYVTPVKNQGQCGSCWAFSATGALEGQMF
              110  ↑    120        130       140         150

160       170        180        190        200
LKTGKLISLSEQNLVDCSHAQGNQGCNGGLMDFAFQYIKENGGLDSEESYPYE
|||:|||||||||||||   |||  ||| ||||||||:||||: :|||||||||||||
RKTGRLISLSEQNLVDCSGPQGNEGCNGGLMDYAFQYVQDNGGLDSEESYPYE
              160        170       180        190        200

210        *        230        240        250
AKDGSCKYRAEFAVANDTGFVDIPQQEKALMKAVATVGPISVAMDASHPSLQF
| : ||||    :  ||||||||||| ||||||||| ||||||||| ||  |  |
ATEESCKYNPKYSVANDTGFVDIPKQEKALMKAVATVGPISVAIDAGHESFLF
              210        *        230        240        250

260        *270       280        290       300         310
YSSGIYYEPNCSSKNLDEGVLLVGYGYEGTDSNKNKYWLVKNSWGSEWGMEGY
|  |||:|| |||   ||||:||||:| |:|  ||||||||||| ||||  ||
YKEGIYFEPDCSSEDMDEGVLVVGYGFESTESDNNKYWLVKNSWGEEWGMGGY
260         270       280        290↑      300         310

320         330
IKIAKDRDNHCGLATAASYPVVN
:| ||||| |:|:||||||| |
VKMAKDRRNHCGIASAASYPTV
         320         330
```

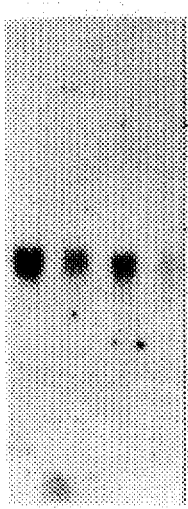
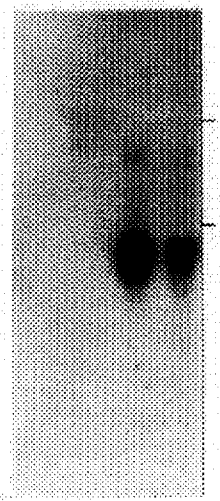
FIG. 3A
a b c d
panel A.
Human probe
human mouse
cells cells
FIG. 3B
a b c d
panel B.
Human probe
human mouse
cells cells
FIG. 3C
a b c d e
panel C.

CLONED CDNA FOR HUMAN PROCATHEPSIN L

This is a continuation of application Ser. No. 07/904,400, filed on Mar. 11, 1992, now abandoned which is a Continuation of Ser. No. 07/154,692, filed Feb. 11, 1988 now abandoned.

FIELD OF THE INVENTION

The present invention is related to a cloned cDNA containing complete coding sequence for the expression of a protein with all properties of the precursor to human procathepsin L. All of the protein's major domains, including the pre, pro, and carboxyterminal extensions are represented in the full length cDNA sequence of the present invention.

BACKGROUND OF THE INVENTION

Cathepsin L is a broad specificity cysteine protease. Tumor cells have been found to secrete proteases including cathepsin L. A mouse clone for cathepsin L has been isolated (Doherty et al, 1985, Mol. Cell. Biol. 5:466–473). However, heretofore, a human procathepsin L clone had not been obtained.

SUMMARY OF THE INVENTION

It is, therefore, an object of the present invention to provide a human cDNA clone for procathepsin L.

It is a further object of the present invention to provide antibodies having specific binding affinity for human procathepsin L.

It is another object of the present invention to provide a kit for detecting procathepsin L in a biological sample.

It is a still further object of the present invention to provide a method for detecting tumor activity by determining the level of procathepsin L in a body sample by the anti-procathepsin L antibodies of the present invention.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 1B and C shows the entire sequence of pHu-16 with the longest open reading frame translated underneath beginning at nucleotide 305 and terminating at nucleotide 1304. The poly A addition signal is underlined.

FIG. 2 shows homology of mouse and human MEP sequences. Complete amino acid sequences deduced for pHu-16 (human MEP) and pMMEP-14 (mouse MEP) are shown. The underlined sequence of mouse MEP corresponds to the N-terminal sequence of secreted MEP purified from mouse tissue culture medium. Arrows indicate where processing occurs, and asterisks indicate potential N-glycosylation sites. The proposed active site amino acids based on papain, cys 136 and his 274, are outlined. Homology is indicated as exact matches (1) and conservative substitutions (:).

FIGS. 3A–C shows Northern blots of RNA from tissue culture cells and human tissues. Panel A and B: Northern blots of 10 µg total RNA from tissue culture cells using two different probes. The sources of RNA were human KB cells (a), multidrug-resistant (MDR) KB cells (b), mouse NIH 3T3 cells (c), and multidrug-resistant NIH 3T3 cells (d). Panel A was hybridized with the human pHU-16 EcoRI fragment and panel B was hybridized with the EcoRI fragment from the mouse MEP clone pMMEP-14. Panel C is a Northern blot using 10 µg total RNA extracted from human kidney (a), normal stomach (b), ovarian carcinoma (c), chondrosarcoma (d), and squamous cell carcinoma of the lung (e). The positions of the 28S and 18S ribosomal RNA markers are indicated.

DETAILED DESCRIPTION OF THE INVENTION

Figure 1A:
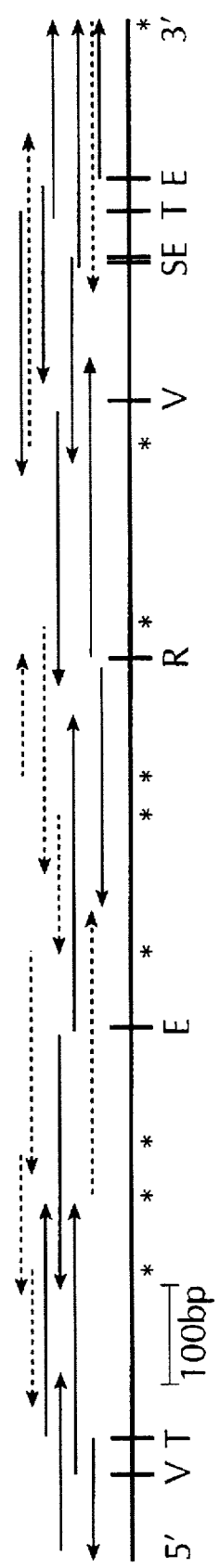
FIG. 1A shows a sequencing strategy for pHu-16. Bold lines are sequences determined using subcloned fragments in pGEM3 or 4 primed with Sp6 and T7 oligonucleotides. The dotted lines indicate sequences derived from the entire pHU-16 plasmid using synthetic oligonucleotides (*) as primers. The orientation of the clone is shown along with some of the restriction sites; V=PvuII, T=TaqI, E=EcoRI, R=RsaI, S=SphI.

The above and various other objects and advantages of the present invention are achieved by the cloned full length cDNA containing a complete coding sequence for the expression of human procathepsin L.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

MATERIALS AND METHODS

Isolation of a human cDNA clone for procathepsin L—The Okayama-Berg cDNA expression library termed GM637, made from mRNA isolated from SV40 transformed human fibroblasts, was obtained from Dr. Hirota Okayama (National Institute of Mental Health, NIH, Bethesda, Md.). 100,000 clones were screened on 20 filters using the standard technique of colony hybridization with the 800 bp EcoRI fragment of mouse major excreted protein (MEP) labeled by nick translation (Lofstrand Laboratories, Gaithersburg, Md.). The filters were washed at moderate stringency conditions: twice with 2×SSC, (1×SSC=0.5M NaCl, 0.015M Na citrate), 1% NaDodSO$_4$ and two times with 0.8×SSC, 1% NaDodSO$_4$ at 60° C. The initial screen yielded 6 potential positive colonies of which three were positive on subsequent screening. The clone designated pHU-16 contained the largest insert (1.6 kb) and was used for all subsequent studies.

Sequencing and Blotting—Sequencing was done using the standard Sanger dideoxy method (Sanger et al. (1978) Proc. Natl. Acad. Sci USA, 74:5463–5467) with the Promega sequencing kit (Promega Biotec, Madison, Wis.) and α-$^{35}$S-dATP at a specific activity of 500 Ci/mmol (NEN, Boston, Mass.). As indicated in the sequencing strategy illustrated in FIG. 1, pHU-16 was sequenced using a combination of two techniques: 1) subcloning regions of pHU-16 DNA into Promega vectors pGEM-3 and pGEM-4 and using Sp6 and T7 primers available from Promega to prime the sequencing reactions; and 2) direct sequencing using 50 ng synthetic oligonucleotides (Applied Biosystems) as primers and the entire pHU-16 cDNA as template.

Quantitation of Human MEP RNA Levels—RNA was isolated from tissue culture cells by standard techniques as described by Chirgwin et al. (1979) *Biochemistry* 18:5294–5299 and Maniatis et al., (1982) *Molecular Cloning: A Laboratory Manual* (Cold Spring Harbor). Standard Northern blots were performed as described by Shen et al., (1986) *Mol. Cell. Biol.* 6:4039–4044. MEP RNA in normal human tissues and cancers was quantitated by slot blot analysis. RNA was first extracted from human tissues. Then only undegraded RNA was used as verified by the pattern of 28S and 18S ribosomal RNAs on agarose gels. Three-fold serial dilution of total RNA (about 0.3 µg to 9 µg) were blotted on nitrocellulose with a Pharmacia slot blot apparatus, and a standard curve was generated for RNA from NIH 3T3 cells transfected with the human MEP clone pHU-16. MEP RNA levels for each sample were determined by comparison with the linear portion of this standard curve and are expressed relative to MEP RNA levels in human KB carcinoma cells (a HeLa subclone) for comparison purposes. Correction for small variations in RNA loading was made using the hybridization signal of a human γ-actin probe obtained from B. Paterson, National Cancer Institute, Bethesda, Md.

Human Procathepsin L Retroviral Expression Vector, DNA Transformations, Enzymatic Activity—A procathepsin L expression vector is constructed by inserting a blunt-ended TaqI fragment of the procathepsin L cDNA into a blunt-ended retroviral vector (pHaMDR1; Ueda et al, (1987) *Proc. Natl. Acad. Sci. USA.* 84:3004–3008) from which the MDR1 gene has been excised with SacII and XhoI. This expression vector (pHaHCL) contains the complete human procathepsin L coding region under control of a murine leukemia virus promoter. pHaHCL (10 µg) is introduced into human A431 cells by co-transfection with 10 µg of the human multidrug-resistance cDNA (pHaMDR1) using calcium phosphate precipitated DNA as described by Shen et al supra with subsequent selection in colchicine (6ng/ml) and amplification of the transferred genes with increasing concentrations of colchicine up to 400 ng/ml. Media from control and pHaHCL transfected cells are assayed for cathepsin L activity with Z-Phe-Arg-NHMec as described by Troen et al 1988 (*J. Biol. Chem.* 263:254–261).

RESULTS

The sequence analysis of human procathepsin L shown in FIG. 1 reveals a single long open reading frame coding for a protein of approximate molecular weight 37,522 daltons. The deduced amino acid sequence was compared to the mouse MEP sequence and some of the features which distinguish the human MEP (procathepsin L) clone from the mouse MEP clone are listed below.

(a) The sequence of nucleotides and the deduced sequence of amino acids are significantly different, although certain cross-hybridization at low stringency is observed. This is illustrated in FIG. 2 which compares the two nucleotide and deduced amino acid sequences.

(b) The mouse clone fails to detect procathepsin L mRNA in human cells. This is illustrated by the results shown in FIG. 3. It is clear, therefore, that the mouse clone cannot be used for identification or diagnostic purposes in humans; only human cDNA being useful for such purposes.

(c) Expression of the human clone in animal cells or bacteria results in the production of a protein which cannot be detected by antibody to the mouse protein. Since the mouse protein fails to produce antibodies which can detect human procathepsin L, it is quite clear that only full-length human clone of the present invention can be employed in order to produce authentic procathepsin L protein to be used as antigen to make antibody having specific binding affinity for human procathepsin L. Such anti-human procathepsin L mono or polyclonal antibodies are produced by standard methodologies well known to one of ordinary skill in the art.

However, two approaches for producing the antibodies are outlined. In the first approach, the human procathepsin L expression vector pHaHCL is transferred by CaPO$_4$-mediated DNA transformation into human A431 cells (ATCC CRL 1555) along with the human MDR1 expression vector, pHaMDR1 (Ueda et al supra). The MDR1 system allows for the selection of cells containing the vectors pHaHCL (retroviral human procathepsin L expression vector) and pHaMDR using colchicine as a selective agent at 6 ng/ml. Pooled colchicine-resistant colonies are selected in increasing concentrations of colchicine up to 400 ng/ml to select for cells carrying amplified pHaMDR1 and pHaHCL cDNAs. These cells express large amounts of human procathepsin L as shown in Table 1.

TABLE 1

| CATHEPSIN L ACTIVITY IN MEDIUM FROM A431 CELLS TRANSFECTED WITH pHaHCL and pHaMDR cDNAs | |
|---|---|
| Cell Line | Cathepsin L activity |
| A431 | 1 |
| A431-pHaHCL-pHaMDR1 | 15 |

Cathepsin L activity is expressed as fluorescence units/$10^6$ cells/sec from medium assayed as described in Troen et al., supra, using the substrate Z-Phe-Arg-NHMec. Medium was collected from cells after 19 hours of exposure.

Human procathepsin L can be purified from the medium of A431-pHaHCL-MDR cells by Sephadex chromatography and HPLC, or by excising human procathepsin L from polyacrylamide gels. This purified material is used as an antigen to inoculate New Zealand white rabbits for polyclonal antibodies and mice to prepare monoclonal antibodies by standard techniques.

In the second approach, a coding segment of the human MEP (procathepsin L) gene is cloned into a bacterial expression vector. The T7 expression system is preferred because it results in the highest yield of protein from cloned segments. A 1136 6bp AvaII-DraI fragment of human MEP is blunt-ended using Klenow polymerase and introduced into the Klenow blunt-ended calf intestinal phosphatase-treated BamH1 site of the T7 expression vector (Studier & Moffatt (1986) *J. Mol. Biol.* 189:113–130). This plasmid (termed pAD 2113) is transformed into the *E. coli* strain HB101 where large quantities of the plasmid can be grown. The isolated plasmid is introduced into the Studier expression strain BL21. Induction for 2 to 3 hours with IPTG results in approximately 10–30% of the bacterial protein being human procathepsin L. This protein after purification on polyacrylamide gel or the like, is then employed as an antigen to prepare polyclonal and monoclonal antibodies by standard techniques.

MEP is known to be an acid protease with amino acid cleavage bond specificity and enzymatic properties identical to cathepsin L. When the human sequence deduced from pHU-16 was compared with the recently published N-terminal amino acid sequence of mature cathepsin L (Mason et al., (1986) *Biochem. J.* 240:370–377), over 98% identity was observed (shown as underlined human sequence in FIG. 2). The two amino acids which are different from the predicted sequence and from the sequence by Mason et al., supra, are Pro for Glu at position 148 and Tyr for Arg at position 153. The position of the N-terminal peptides of mature human cathepsin L within the deduced amino acid sequence of human procathepsin L indicate the sites at which this precursor to human procathepsin L is processed to the lower molecular weight mature forms.

Expression of Human Procathepsin L mRNA in Normal Tissues and Tumors—FIG. 3 shows the result of Northern blots with human KB (HeLa) cells and NIH 3T3 mouse cell RNA probed with the EcoRI 800 bp fragment from the mouse and human MEP cDNA clones. The human probe recognized a 1.6–1.8 kb cathepsin L message in human KB cells which migrated just below the 18S RNA marker (FIG. 3A) and appeared to be the same size as MEP mRNA from mouse cells (FIG. 3B). At high stringency, the mouse probe recognized a 1.6 kb–1.8 kb RNA in mouse cells but no message in human cells (FIG. 3B). Human tissue samples from various sources were used to isolate RNA for Northern blots and the filters were probed with the EcoRI fragment of the human procathepsin L cDNA. The same 1.6 kb–1.8 kb RNA was found in all human tissues tested (examples shown in FIG. 3C).

Quantitative Assay of Human Procathepsin L mRNA in Normal Tissues and Tumors—FIG. 3 shows the expression of human MEP/cathepsin L RNA in several normal human tissues and tumors. Quantitation of MEP RNA levels by slot blot analysis is shown in Table 1. All human tissues had easily detectable levels of MEP/cathepsin L mRNA. Among normal tissues, a 10-fold variation in RNA levels was found with spleen, liver, lung and kidney having the highest level. A wider variation was found among tumors (20-fold), with tumors on the average expressing more MEP/cathepsin L RNA than normal tissues. Among the samples tested, pancreatic tumor (endocrine and exocrine), genitourinary tumors, sarcomas and squamous cell carcinomas had the highest levels of expression of MEP mRNA.

A method for determining the level of mRNA for human procathepsin L in a biological sample, comprises reacting mRNA present in said biological sample and a known amount of procathepsin L mRNA as a standard, with the cloned cDNA of present invention and determining the level of hybridization between the cloned cDNA, and mRNA from the biological sample and the standard, the differential relative level of hybridization between said sample and the standard being indicative of the amount of procathepsin L mRNA in said biological sample.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An isolated cDNA molecule encoding human procathepsin L wherein said nucleic acid sequence comprises the nucleic acid sequence shown in FIG. 1.

2. An isolated cDNA molecule encoding human procathepsin L wherein said procathepsin L comprises the amino acid sequence shown in FIG. 1.

3. An expression vector comprising the cDNA molecule of claim 1 or 2.

4. The expression vector of claim 3, wherein said vector is a retroviral expression vector.

5. The expression vector of claim 3, wherein said vector is a bacterial expression vector.

6. The expression vector of claim 5, wherein said vector is a T7 expression vector.

7. A host cell containing said expression vector according to claim 3.

8. The host cell of claim 7, wherein said cell is an animal cell.

9. The host cell of claim 7, wherein said cell is a A431 (ATCC 1555) human cell.

TABLE 2

RELATIVE MEP mRNA LEVELS IN HUMAN TISSUES AND TUMORS*

| Low (<.5) | | Moderate (.5–1.1) | | High (>1.1) | |
|---|---|---|---|---|---|
| normal esophagus | (.1) | normal spleen | (1.1) | pancreas, adenocarcinoma | (3.6) |
| normal stomach | (.2) | normal liver | (.7, 1.0) | renal cell carcinoma | (1.5) |
| normal jejunum | (.3) | normal lung | (.6) | chondrosarcoma | (1.4) |
| normal colon | (.3) | normal kidney | (.5) | sarcoma | (1.2) |
| normal ovary | (.2) | adrenal cancer | (.2, .5, .7, .8) | testicular cancer | (1.4) |
| normal adrenal | (.3) | kidney, transitional cell | (1.1) | ovarian cancer | (.2, .7, .9, 1.6, 2.2) |
| lung, adenocarcinoma | (.2) | bladder, carcinoma | (.5, .6) | parathyroid carcinoma | (1.2) |
| lung, mesothelioma | (.2) | insulinoma | (.7) | lung, squamous cell carcinoma | (.6, 1.6, 1.6) |
| lymphoma | (.2, .3) | glucagonoma | (.8) | neck, squamous cell carcinoma | (1.4) |
| pheochromocytoma | (.3, .4, .5) | | | | |
| prostate, adenocarcinoma | (.3, .5) | | | | |
| thyroid adenoma | (.2, .3) | | | | |

*The numbers in parenthesis represent different tissue samples assayed for MEP/cathepsin L RNA levels as described in Materials and Methods and compared to the MEP RNA level of KB carcinoma cells, taken as 1.

Of course, a kit for determining the presence and the level of procathepsin L in a biological sample is now made possible. Such a kit comprises a container containing the cDNA for human procathepsin L for identification, detection or quantitation of the mRNA for procathepsin L by such conventional techniques as in situ hybridization, Northern blot analysis and the like.

10. The host cell of claim 7, wherein said cell is a bacterial cell.

11. The host cell of claim 7, further comprising a multiple drug resistance gene introduced into said cell.

12. The cell of claim 11, wherein said multiple drug resistance gene is pHAMDR1.

\* \* \* \* \*